United States Patent
Eickhoff et al.

(10) Patent No.: US 7,174,766 B2
(45) Date of Patent: Feb. 13, 2007

(54) CALIBRATION DEVICE FOR CARBON DIOXIDE SENSOR

(75) Inventors: Steven J. Eickhoff, Plymouth, MN (US); Roland A. Wood, Bloomington, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/908,737

(22) Filed: May 24, 2005

(65) Prior Publication Data

US 2006/0266096 A1    Nov. 30, 2006

(51) Int. Cl.
  *G12B 13/00*    (2006.01)
  *G01N 21/417*    (2006.01)
(52) U.S. Cl. .................. 73/1.03; 73/1.06; 73/1.88; 73/31.02; 73/31.05
(58) Field of Classification Search ........ 73/1.01–1.03, 73/1.06, 1.07, 1.88, 23.31, 31.01–31.03, 73/31.05
See application file for complete search history.

(56) References Cited

U.S. PATENT DOCUMENTS

| | | | |
|---|---|---|---|
| 3,904,486 A | 9/1975 | Faurschou et al. | |
| 4,025,412 A | 5/1977 | LaConti | |
| 4,123,700 A | 10/1978 | LaConti et al. | |
| 4,171,253 A | 10/1979 | Nolan et al. | |
| 4,851,088 A | 7/1989 | Chandrasekhar et al. | |
| 5,322,612 A | 6/1994 | Abe et al. | |
| 5,668,302 A | 9/1997 | Finbow et al. | |
| 6,358,384 B1 * | 3/2002 | Warburton | 204/427 |
| 6,456,943 B1 | 9/2002 | Kogure et al. | |
| 6,632,674 B1 | 10/2003 | Warburton | |
| 6,948,352 B2 | 9/2005 | Rabbett et al. | |
| 2002/0157447 A1 | 10/2002 | Schell | |
| 2003/0145644 A1 | 8/2003 | Rabbett et al. | |
| 2004/0018632 A1 | 1/2004 | Shabana et al. | |
| 2004/0050142 A1 | 3/2004 | Hok | |
| 2004/0158410 A1 | 8/2004 | Ono et al. | |
| 2004/0206906 A1 | 10/2004 | Owen | |
| 2005/0262924 A1 | 12/2005 | Wood et al. | |

FOREIGN PATENT DOCUMENTS

| | | |
|---|---|---|
| DE | 3939166 | 5/1991 |
| DE | 10220668 A1 * | 11/2003 |
| EP | 0355896 | 2/1990 |

(Continued)

OTHER PUBLICATIONS

"TGS 4160 Carbon Dioxide Sensor", Oct. 2000, Figaro, pp. 1-2.*

(Continued)

*Primary Examiner*—Hezron Williams
*Assistant Examiner*—David A. Rogers
(74) *Attorney, Agent, or Firm*—Kris T. Fredrick

(57) ABSTRACT

A self-calibrating carbon dioxide sensor that includes a carbon dioxide detector and a carbon dioxide gas generator. In some embodiments, the carbon dioxide gas generator includes a heating element and a carbon dioxide gas releasing solid material in thermal communication with the heating element. The carbon dioxide gas releasing solid material releases carbon dioxide when heated by the heating element. Methods of calibrating a self-calibrating carbon dioxide sensor are also disclosed.

18 Claims, 1 Drawing Sheet

FOREIGN PATENT DOCUMENTS

| | | | |
|---|---|---|---|
| EP | 0890837 | | 1/1999 |
| GB | 1217625 | | 12/1970 |
| GB | 1398977 | A * | 6/1975 |
| GB | 2356708 | | 5/2001 |
| JP | 03123848 | A * | 5/1991 |
| JP | 08220063 | A * | 8/1996 |
| JP | 08220064 | | 8/1996 |
| WO | 9917110 | | 4/1999 |
| WO | 03056325 | | 7/2003 |

OTHER PUBLICATIONS

Pinkerton et al., "Bottling the Hydrogen Genie," The Industrial Physicist, vol. 10, No. 1, 5 pages, Feb./Mar. 2004.

* cited by examiner

CALIBRATION DEVICE FOR CARBON DIOXIDE SENSOR

BACKGROUND

This disclosure relates to a calibration device for a carbon dioxide sensor. In particular, this disclosure related to internal generation of a carbon dioxide reference gas to calibrate a carbon dioxide sensor.

Instruments and transducers for the measurement of carbon dioxide ($CO_2$) concentration in air have been described in the patent literature, and also in the form of commercially available products on the market. Many of these instruments are based on the absorption spectra within the infrared wavelength area of electromagnetic radiation of the $CO_2$ molecule. Such spectra can be detected and analyzed by spectroscopic instruments according to known technology. By measuring at specific wavelengths where the absorption of $CO_2$ deviates from other constituents of air, it is possible to extract an output signal with required sensitivity and specificity.

Other instruments are based on solid electrolyte or an electrochemical cell that uses a catalytic electrode so that the carbon dioxide is either oxidized or reduced with the exchange of electrons. The flow of current due to the oxidation or reduction of the carbon dioxide is then detected as a measure of the concentration of the detected carbon dioxide. However, one problem with carbon dioxide sensors is that they lose sensitivity over time. For example, the working life of an electrochemical cell is determined by the activity of the cell's catalytic electrode that is used to detect carbon dioxide within the sensor. This activity is gradually reduced over time by contaminant gases and poisons such that the sensitivity of the sensor drifts downward.

If the instrument into which the carbon dioxide sensor is built is calibrated regularly, this downward sensitivity drift can be compensated for by adjusting the gain of the carbon dioxide sensor, and any faulty carbon dioxide sensors can be replaced immediately. However, if the instrument is in a difficult position to service, or if calibration of the carbon dioxide sensor is not otherwise freely available, it is often impossible to confirm that the carbon dioxide sensor is functioning correctly. Therefore, as the carbon dioxide sensor reaches the end of its working life, the output of the sensing cell may be insufficient to generate an alarm or other condition. As a result, a situation could arise where toxic levels of gas are present, but the carbon dioxide sensor is incapable of providing the requisite warning.

SUMMARY

A self-calibrating carbon dioxide sensor is disclosed. The sensor includes a carbon dioxide detector and a carbon dioxide gas generator. In one illustrative embodiment, the carbon dioxide gas generator includes a heating element and a carbon dioxide gas releasing solid material adjacent to the heating element. The carbon dioxide gas releasing solid material releases carbon dioxide when heated by the heating element.

In another embodiment, a self-calibrating carbon dioxide sensor includes a sensor housing, a carbon dioxide detector disposed within the sensor housing, and a carbon dioxide gas generator disposed within the senor housing. The carbon dioxide gas generator includes a heating element and a carbon dioxide gas releasing solid material adjacent to the heating element. The carbon dioxide gas releasing solid material releases a known amount of carbon dioxide reference gas when heated by the heating element.

An illustrative method of calibrating a carbon dioxide sensor is also disclosed. The illustrative method includes providing a carbon dioxide detector and a carbon dioxide gas generator adjacent to the carbon dioxide detector. The carbon dioxide gas generator includes a heating element and a carbon dioxide gas releasing solid material adjacent to the heating element. Then the method includes, heating the carbon dioxide gas releasing solid material with the heating element to release a known amount of carbon dioxide gas and detecting the known amount of carbon dioxide gas with the carbon dioxide detector to provide an output value from the carbon dioxide detector. The output value is then calibrated based on the known amount of carbon dioxide gas released.

The above summary of the present invention is not intended to describe each disclosed embodiment or every implementation of the present invention. The Figures, and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
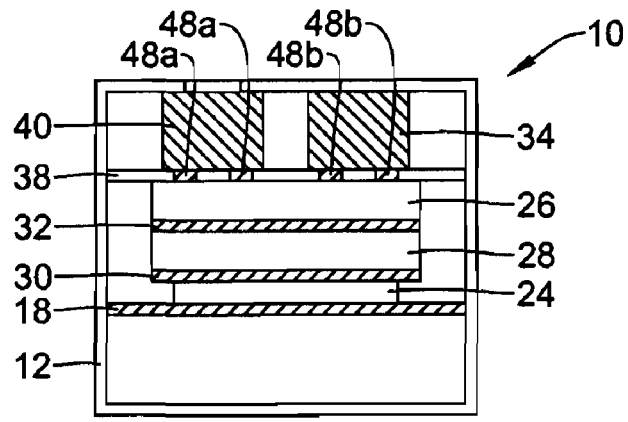
FIG. 1 is a schematic cross-sectional view of an illustrative self-calibrating carbon dioxide sensor.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention. The Figures are not drawn to any particular scale and are simply presented for ease of illustration.

DETAILED DESCRIPTION

This disclosure relates to a calibration device for a carbon dioxide sensor. In particular, this disclosure related to internal generation of a carbon dioxide reference gas to calibrate a carbon dioxide sensor. In many embodiments, a self-calibrating carbon dioxide sensor includes a sensor housing, a carbon dioxide detector disposed within the sensor housing, and a carbon dioxide gas generator disposed within the senor housing. The carbon dioxide gas generator can include a heating element and a carbon dioxide gas releasing solid material adjacent to the heating element. The carbon dioxide gas releasing solid material releases a known amount of carbon dioxide reference gas when heated by the heating element. The sensor can be calibrated based on the known amount of carbon dioxide released by the carbon dioxide gas generator.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention.

The recitation of numerical ranges by endpoints includes all numbers subsumed within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. Thus, for example, reference to "a heating element" includes two or more heating elements. As used in this specification and the appended claims, the term "or" is generally employed in its sense including "and/or" unless the content clearly dictates otherwise.

As shown in FIG. 1, a self-calibrating carbon dioxide sensor 10 has a sensor housing 12 that can substantially surround a carbon dioxide detector 22 and a carbon dioxide gas generator 34. In some embodiments, the sensor housing 12 can be formed of a metal, but this is not required. In one embodiment, the sensor housing 12 is formed of nickel plated steel.

In some embodiments, the carbon dioxide detector 22 is supported by a support plate 18 disposed within the sensor housing 12. In some embodiments, the carbon dioxide detector 22 is in the form of an electrochemical cell.

The illustrated carbon dioxide detector 22 includes lower and upper cell plates 24 and 26, a solid electrolyte membrane 28, and lower and upper catalyst electrodes 30 and 32. The lower and upper cell plates 24 and 26, may for example, be hydrophobic Teflon™ disks, but this is not required. In this illustrated embodiment, the lower cell plate 24 is sandwiched between the support plate 18 and lower catalyst electrode 30, the lower catalyst electrode 30 is sandwiched between the solid electrolyte membrane 28 and the lower cell plate 24, and the upper catalyst electrode 32 is sandwiched between the solid electrolyte membrane 28 and the upper cell plate 26. The catalyst electrode 30 and 32, may for example, include an element from the group Au, Pt, Pd, Ru, Rh, Ir, Os, Ag, etc., or an alloy or mixture of the elements from this group, or porous elements of the group mixed with carbon black, or porous elements of the group mixed with carbon black and Nafion particles. The solid electrolyte membrane 28 may be, for example, Nafion or Nafion composite like Nafion/7SiO$_2$-2P$_2$O$_5$—ZrO$_2$, and Nafion/ZrP particles or the Sandia Polymer Electrolyte Alternative (SPEA) for higher temperature applications. Illustrative electrochemical carbon dioxide gas detectors 22 may be of the type shown in one or more of U.S. Pat. Nos. 4,851,088 and 5,322,612 and U.S. Patent Application Publication No. 2004/0158410, all of which are incorporated by reference herein.

In some embodiments, the carbon dioxide detector 22 is in the form of an infrared (IR) carbon dioxide sensor. Illustrative IR carbon dioxide sensors are described in U.S. Pat. No. 6,456,943 and U.S. Patent Application Publication Nos. 2002/0157447, 2004/0050142, and 2004/0206906, all of which are incorporated by reference herein.

A carbon dioxide gas generator 34 or reference gas generator 34 generates a carbon dioxide reference gas that is provided to the carbon dioxide detector 22 so that the carbon dioxide detector can be self-calibrated. In many embodiments, the carbon dioxide gas generator 34 generates a known amount of carbon dioxide within the sensor housing 12 and the known amount of carbon dioxide is detected by the carbon dioxide detector 22.

In some embodiments, the carbon dioxide gas generator 34 includes a carbon dioxide gas generating chamber 36 (see FIG. 2) and a gas diffusion control plate 38. In some embodiments, the gas sensor 10 also includes an active charcoal filter 40. The gas diffusion control plate 38 can separate the carbon dioxide gas generating chamber 36 and the optional active charcoal filter 40 from the carbon dioxide detector 22 and abuts the upper cell plate 26 on an electrochemical carbon dioxide detector 22 or abuts an IR sensing chamber of an IR carbon dioxide detector (not shown).

Figure 2:
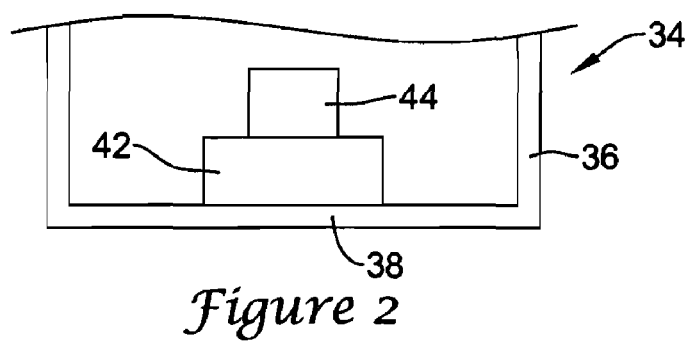
FIG. 2 is a schematic cross-sectional view of the reference gas generator of the self-calibrating gas sensor shown in FIG. 1.

As shown in FIG. 2, the carbon dioxide gas generating chamber 36 houses a heating element 42 and a carbon dioxide gas releasing solid material 44 that is in proximity to, adjacent to, in contact with, or otherwise thermally coupled to, the heating element 42. The carbon dioxide gas releasing solid material 44, when heated, produces the carbon dioxide reference gas.

In many embodiments, the carbon dioxide gas releasing solid material 44 includes a Group 2 carbonate material that, when the heating element 42 is energized, is heated to a known temperature and consequently thermally decomposes the carbon dioxide gas releasing solid material to produces a known amount of carbon dioxide. In some embodiments, the carbon dioxide gas releasing solid material is heated to a temperature in a range from 200 to 1500° C., or from 200 to 1000° C., or from 250 to 500° C., or from 500 to 1500° C., or from 750 to 1250° C. An overpressure of carbon dioxide reference gas then can flow through holes 48$b$ in the gas diffusion control plate 38 directly onto the carbon dioxide detector 22.

In many embodiments, the Group 2 carbonate material includes beryllium carbonate (BeCO$_3$), magnesium carbonate (MgCO$_3$), calcium carbonate (CaCO$_3$), strontium carbonate (SrCO$_3$), barium carbonate (BaCO$_3$), or radium carbonate (RaCO$_3$). In some embodiments, the Group 2 carbonate material includes magnesium carbonate (MgCO$_3$) or calcium carbonate (CaCO$_3$). In other embodiments, the carbon dioxide gas releasing solid material is not a Group 2 carbonate. In these embodiments, the carbon dioxide gas releasing solid material may include copper carbonate (CuCO$_3$).

When the self-calibration gas sensor 10 is to be calibrated, the heater 42 is energized to heat the material 44 to a predetermined temperature and for a predetermined time that causes the material 44 to release an overpressure of carbon dioxide reference gas which is supplied to the gas detector 22. The gas detector 22 senses the reference gas and generates a reference signal between the lower and upper catalyst electrodes 30 and 32. This signal is used to perform self-calibration of the sensor 10. After such self-calibration, the heater 42 is de-energized so that the overpressure of the reference gas falls to a negligible level.

Self-calibration of the self-calibration gas sensor 10 can be intermittently repeated as desired. In many embodiments, the carbon dioxide gas releasing solid material can be reheated with the heating element to release a subsequent known amount of carbon dioxide gas. These subsequent known amounts of carbon dioxide gas can be detected and used to recalibrate the output value of the carbon dioxide detector. In some embodiments, a time interval of at least a day, a week, a month, or a year occurs between the heating step and reheating step.

As shown in FIG. 1, the sensor housing 12 forms a continuous housing that houses the gas detector 22 and the reference gas generator 34. Accordingly, in this construction of the present invention, the gas detector 22 and the reference gas generator 34 are not housed in separate and separated housings.

Figure 3:
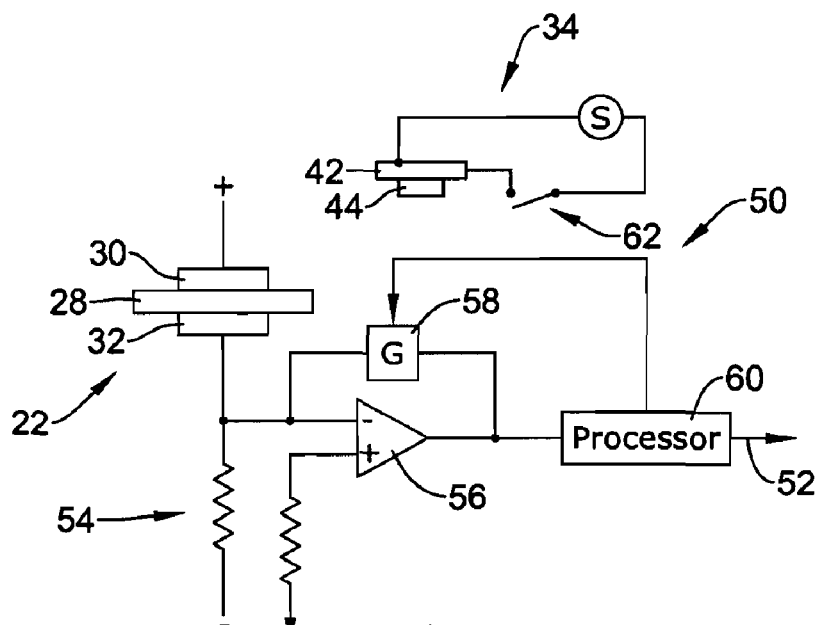
FIG. 3 is a diagrammatic circuit that can be used with an illustrative self-calibrating carbon dioxide sensor.

As shown in FIG. 3, a controller 50 provides an output 52 based on the carbon dioxide detected by the gas detector 22. The controller 50 may also control the reference gas generator 34 to calibrate the gas detector 22. The output 52 may be coupled to various devices. For example, the output 52 may be coupled to an alarm indicator to produce a warning when the level of the detected carbon dioxide gas exceeds a predetermined limit, or the output 52 may be coupled to an apparatus such as a ventilator to control the effects of the gas being detected. The self-calibration could be pre-programmed to operate on a schedule such as, for example, twice a year or once a year. Calibration could also be initiated through pushing an external button. When self-calibration is in process, the controller 50 can provide an alarm/warning that self-calibration is being performed, and that the controller 50 may be out of function momentarily.

In the illustrated embodiment, the lower and upper catalyst electrodes 30 and 32 are coupled between the terminals of a voltage source through a resistor 54. The junction between the resistor 54 and the gas detector 22 is coupled to an amplifier 56 having a gain controlling element 58 in a feedback circuit around the amplifier 56. The output of the amplifier 56 is coupled to a processor 60 that provides the output 52. The processor 60 may also control a switch 62 to selectively connect a source S to the heater 42 so as to energize the reference gas generator 34.

During normal operation, the processor 60 provides the output 52 based on the output of the amplifier 56 and controls the switch 62 so that the switch 62 is open. Thus, the reference gas generator 34 is de-energized and the output 52 indicates the level of ambient gas normally being detected by the gas detector 22. This ambient gas normally being detected by the gas detector 22 enters the gas sensor 10 through one or more suitable holes (not shown) in the sensor housing 12, flows through the optional active charcoal filter 40, then flows through one or more holes 48a of the gas diffusion control plate 38 into the gas detector 22.

During self-calibration, the processor 60 controls the switch 62 so that the switch 62 is closed. Thus, the reference gas generator 34 is energized to produce the carbon dioxide reference gas and to provide the reference gas to the gas detector 22 as described above. The processor 60 receives the output of the amplifier 56 and may change one or more calibration parameters. Once the calibration procedure is complete, and during subsequent normal gas sensing operation, the processor 60 may use the one or more calibration parameters to provide a calibrated output 52 that compensates for any change to sensitivity or other changes to the gas sensor. Accordingly, the self-calibration gas sensor 10 is calibrated.

The controller 50 may intermittently repeat the above described calibration as many times as necessary or desired. The time periods between such repeated calibrations may be periodic or aperiodic and may be of any length as desired.

In many embodiments, the circuit 50 can be mounted as a chip or otherwise on a board or other support within the sensor housing 12. The output 52 may then be run to the exterior of the sensor housing 12.

FIG. 1 illustrates an embodiment where the sensor housing 12 forms a continuous housing that houses the gas detector 22 and the reference gas generator 34. However, the gas detector 22 and the reference gas generator 34 may instead be housed in separate and separated housings, as desired.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A self-calibrating article comprising:
   a carbon dioxide gas detector and a carbon dioxide gas generator;
   wherein the carbon dioxide gas generator includes a heating element and a carbon dioxide gas releasing solid material in thermal communication with the heating element, and wherein the carbon dioxide gas generator is configured to heat the heating element, to a predetermined temperature for a predetermined time such that carbon dioxide gas releasing solid material releases a known amount of carbon dioxide reference gas; and
   wherein the self-calibrating article utilizes the known amount of carbon dioxide reference gas to calibrate the carbon dioxide gas detector.

2. A self-calibrating article according to claim 1 wherein the carbon dioxide gas releasing solid material includes a Group 2 carbonate.

3. A self-calibrating article according to claim 1 wherein the carbon dioxide gas releasing solid material includes magnesium carbonate or calcium carbonate.

4. A self-calibrating article according to claim 1 wherein the carbon dioxide gas releasing solid material is disposed on the heating element.

5. A self-calibrating article according to claim 1 further comprising a housing, wherein the carbon dioxide detector and the carbon dioxide gas generator are disposed within the housing.

6. A self-calibrating article according to claim 1 wherein the carbon dioxide detector comprises an infrared carbon dioxide detector.

7. A self-calibrating article according to claim 1 wherein the carbon dioxide detector, comprises an electrochemical carbon dioxide detector.

8. A self-calibrating article according to claim 1 wherein the carbon dioxide detector is disposed adjacent to the carbon dioxide gas generator.

9. A self-calibrating article according to claim 1 further comprising a processor configured to calibrate the carbon dioxide detector based on an amount of carbon dioxide detected by the carbon dioxide detector when exposed to at least some of the known amount of carbon dioxide released by the carbon dioxide gas generator.

10. A self-calibrating article according to claim 9 wherein the processor includes one or more calibration parameters, the processor configured to control the carbon dioxide gas generator to heat the heating element and release the known amount of carbon dioxide, the processor further configured to receive an output signal from the carbon dioxide detector when the carbon dioxide detector is exposed to at least some of the known amount of released carbon dioxide and make changes to the one or more calibration parameters based on the output signal from the carbon dioxide detector.

11. A self-calibrating article according to claim 9 wherein the processor causes a known amount of energy to be applied to the heating element to release the known amount of carbon dioxide.

12. A self-calibrating carbon dioxide gas sensor comprising:
- a sensor housing, a carbon dioxide gas detector disposed within the sensor housing, and a carbon dioxide gas generator disposed within the housing;
- wherein the carbon dioxide gas generator includes a heating element and a carbon dioxide gas releasing solid material in thermal communication with the heating element, and wherein the carbon dioxide gas releasing solid material releases a known amount of carbon dioxide reference gas when heated by the heating element; and
- wherein self-calibrating carbon dioxide gas sensor utilizes the known amount of carbon dioxide reference gas to calibrate the carbon dioxide gas detector.

13. A self-calibrating carbon dioxide gas sensor according to claim 12 wherein the carbon dioxide gas releasing solid material includes a Group 2 carbonate.

14. A self-calibrating carbon dioxide gas sensor according to claim 12 wherein the carbon dioxide gas releasing solid material is disposed on the heating element.

15. A self-calibrating carbon dioxide gas sensor according to claim 12 wherein the carbon dioxide detector comprises an infrared carbon dioxide detector.

16. A self-calibrating carbon dioxide gas sensor according to claim 12 wherein the carbon dioxide detector comprises an electrochemical carbon dioxide detector.

17. A self-calibrating carbon dioxide gas sensor according to claim 12 further comprising a processor configured to calibrate the carbon dioxide detector based on a detected amount of the known amount of carbon dioxide reference gas released by the carbon dioxide gas generator.

18. A self-calibrating carbon dioxide gas sensor according to claim 17 wherein the processor includes one or more calibration parameters, the processor configured to control the heating element to release the known amount of carbon dioxide, the processor configured to receive an output signal from the carbon dioxide detector and make changes to the one or more calibration parameters based on the output signal.

* * * * *